(12) United States Patent
Bender et al.

(10) Patent No.: US 8,530,644 B2
(45) Date of Patent: Sep. 10, 2013

(54) METHOD FOR REMOVING IMPURITIES FROM BIOPOLYMER MATERIAL

(75) Inventors: Johannes Caspar Mathias Elizabeth Bender, Utrecht (NL); Pieter Sebastiaan Vermeulen, Utrecht (NL)

(73) Assignee: Bender Analytical Holding B.V., Utrecht (NL)

( * ) Notice: Subject to any disclaimer, the term of this patent is extended or adjusted under 35 U.S.C. 154(b) by 379 days.

(21) Appl. No.: 12/999,565

(22) PCT Filed: Jun. 19, 2008

(86) PCT No.: PCT/NL2008/050396
§ 371 (c)(1),
(2), (4) Date: Jan. 20, 2011

(87) PCT Pub. No.: WO2009/154440
PCT Pub. Date: Dec. 23, 2009

(65) Prior Publication Data
US 2011/0168635 A1     Jul. 14, 2011

(51) Int. Cl.
*C07H 1/06*     (2006.01)
*C07H 1/08*     (2006.01)

(52) U.S. Cl.
USPC ........................................................ 536/127

(58) Field of Classification Search
None
See application file for complete search history.

(56) References Cited

U.S. PATENT DOCUMENTS

| | | |
|---|---|---|
| 3,978,209 A | 8/1976 | Limjuco et al. |
| 4,808,314 A * | 2/1989 | Karplus et al. ............ 210/638 |
| 5,589,591 A | 12/1996 | Lewis |
| 6,451,772 B1 | 9/2002 | Bousman et al. |
| 6,891,037 B1 | 5/2005 | Hasler et al. |

FOREIGN PATENT DOCUMENTS

| | | |
|---|---|---|
| EP | 0 072 513 A2 | 2/1983 |
| WO | WO93/13136 | 7/1993 |
| WO | WO00/09566 | 2/2000 |
| WO | WO 2004/080343 A2 | 9/2004 |

OTHER PUBLICATIONS

Adam, O. et al. "A Nondegradative Route for the Removal of Endotoxin from Exopolysaccharides". Analytical Biochemistry, 1995, vol. 225, pp. 321-327.
Petsch, D. et al. "Endotoxin removal from protein solutions." Journal of Biotechnology, 2000, vol. 76, pp. 97-119.
International Search Report mailed Feb. 26, 2009 in PCT/NL2008/050396.
International Preliminary Report on Patentability mailed Sep. 9, 2010 in PCT/NL2008/050396.
Hirayama et al., Chromatographic removal of endotoxin from protein solutions by polymer particles, Journal of Chromatography B, 781, 2002, pp. 419-432.

* cited by examiner

*Primary Examiner* — Layla Bland
(74) *Attorney, Agent, or Firm* — Gilberto M. Villacorta; Sunit Talapatra; Foley & Lardner LLP

(57) ABSTRACT

The present invention relates to a method for removing impurities from biopolymer material, e.g. polysaccharides, polypeptides or polynucleotides. More particularly, the present invention provides a method of reducing lipopolysaccharide levels in a lipopolysaccharide containing biopolymer material, comprising the successive steps of: a) providing an aqueous solution containing 0.05-50 wt. % of dissolved lipopolysaccharide-containing biopolymer material; 0.001-10 wt.% of a surfactant; 0.05-15 wt. % of solid adsorbent; and at least 50 wt. % of water; b) allowing the adsorbent to adsorb lipopolysaccharides; c) separating the solid adsorbent containing adsorbed lipopolysaccharides from the remaining aqueous solution; and d) recovering the biopolymer material containing a reduced level of lipopolysaccharide from the separated aqueous solution.

13 Claims, No Drawings

METHOD FOR REMOVING IMPURITIES FROM BIOPOLYMER MATERIAL

TECHNICAL FIELD OF THE INVENTION

The present invention relates to a method for removing endotoxins, such as lipopolysaccharides, from biopolymer material, e.g. polysaccharides, polypeptides or polynucleotides. The method of the present invention enables the manufacture of biopolymer materials containing extremely low levels of lipopolysaccharides. The present method is very robust and does not require sophisticated, capital intensive equipment.

BACKGROUND OF THE INVENTION

Lipopolysaccharides are potential endotoxins, i.e. toxic, natural compounds found inside pathogens such as bacteria. Classically, an "endotoxin" is a toxin, which unlike an "exotoxin", is not secreted in soluble form by live bacteria, but is a structural component in the bacteria which is released mainly when bacteria are lysed.

Lipopolysaccharide (LPS) or lipo-oligo-saccharide (LOS) is a prototypical example of an endotoxin that is found in the outer membrane of various gram-negative bacteria. The term LPS is often used interchangeably with endotoxin, owing to its historical discovery. In the 1800s it became understood that bacteria could secrete toxins into their environment, which became broadly known as "exotoxin". The term endotoxin came from the discovery that portions of gram-negative bacteria itself can cause toxicity, hence the name endotoxin. Studies of endotoxin over the next 50 years revealed that the effects of "endotoxin" was in fact due to lipopolysaccharide. The only gram-positive bacteria known to produce endotoxin is *Listeria monocytogenes*.

LPS consist of a polysaccharide (sugar) chain and a lipid moiety, known as lipid A, which is responsible for the toxic effects. The polysaccharide chain is highly variable amongst different bacteria. LPSs are approximately 10 kDa in size but can form large aggregates up to 1000 kDa. Humans are able to produce antibodies to LPSs after exposure but these are generally directed at the polysaccharide chain and do not protect against a wide variety of endotoxins. Injection of a small amount of LPS in human volunteers produced fever, a lowering of the blood pressure, and activation of inflammation and coagulation. LPSs are in large part responsible for the dramatic clinical manifestations of infections with pathogenic gram-negative bacteria, such as *Neisseria meningitidis*, the pathogen that causes fulminant meningitis.

In pharmaceutical production, it is necessary to remove LPSs from drug product containers as even small amounts of this endotoxin will cause illness, but not disease, in humans. Usually, a depyrogenation oven is used for this purpose. Temperatures of approximately 400° C. are required to break down this substance. Based on primary packaging material as syringes or vials a glass temperature of 250° C. and a holding time of 30 min is typical to achieve 3 log reduction on endotoxin levels.

Likewise, it must be ensured that endotoxins are removed from pharmaceutical grade biopolymers, such as alginate, xanthan gum and gelatine. To this end several methods have been proposed in the prior art.

WO 93/13136 describes a process for purifying polysaccharides comprising:
    filtering a polysaccharide solution having a concentration of less than 1% through a first nitrocellulose filter having a pore size of at least 45 microns;
    filtering the resulting solution through a second nitrocellulose filter having a pore size of less than 12 microns;
    filtering the resultant solution through a membrane having a pore size less than 12 microns, said membrane modified with polypeptides to bind hydrophobic impurities; and
    dialyzing the resulting solution with a membrane having a lower molecular weight cut-off than the first ultra-filtration membrane.

The process described in WO 93/13136 is not suitable for processing viscous solutions and is not very robust.

U.S. Pat. No. 5,589,591 describes a method of making a highly purified, substantially endotoxin-free arabinogalactan composition which comprises the steps of:
    (i) removing from an arabinogalactan-containing preparation by ultrafiltration, materials of a molecular weight that are less than the molecular weight of the arabinogalactan composition, and collecting the arabinogalactan-containing fraction thereof;
    (ii) thereafter removing from the arabinogalactan-containing fraction by ultrafiltration, endotoxin and materials of a molecular weight that are greater than the molecular weight of the arabinogalactan; and
    (iii) collecting the resulting arabinogalactan-containing fraction, which has been rendered substantially endotoxin-free.

What has been said above in relation to WO 93/13136 equally applies to this US patent.

WO 00/09566 describes a method for obtaining ultra-pure alginate, said method comprising the steps of:
    extracting a dissolved material consisting of algae or raw alginate using a complexing agent such EDTA or activated carbon;
    filtering the solution;
    precipitating the alginate contained in the solution; and
    recovering the precipitated alginate.

WO 00/09566 also describes an embodiment in which prior to filtration cellular components and particles are sedimented with the aid of porous binding agents such as kieselguhr, cellulose or recycling materials from renewable sources. The process described in the international patent application suffers from the drawback that the porous binding agents are difficult to precipitate from viscous fluids, even at increased centrifugal force. If such viscous fluids additionally exhibit a high specific density, it is nearly impossible to separate the insoluble material from the aquous phase.

U.S. Pat. No. 6,451,772 discloses a method for preparing a biopolymer composition comprising a salt of a biopolymer having an endotoxin content less than about 100 endotoxin units per gram comprises the steps of
    (i) contacting an aqueous solution of a biopolymer salt with a hydrophobic material, such as polystyrene, polypropylene or fluorocarbon polymers, to adsorb endotoxin on said material; and
    (ii) precipitating the biopolymer salt having an endotoxin content less than about 100 endotoxin units per gram from the solution by mixing a water miscible organic solvent with the solution.

The US patent also discloses a method in which the precipitation step is replaced by a liquid-liquid extraction using a water immiscible solvent. Furthermore, it is mentioned that in case of alginates the aqueous biopolymer solution may be contacted with activated carbon to remove polyphenols. Important drawbacks of the method described in U.S. Pat. No. 6,451,772 are that (i) it is virtually impossible to avoid co-precipitation of the biopolymer salt and the hydrophobic material upon addition of the water miscible organic fluid and (ii) poor mass transfer during liquid-liquid extraction.

EP-A 0 072 513 describes a process for the preparation of an antigenic capsular bacterial polysaccharide from a culture medium or a solution comprising at least one precipitation step by formation of a complex between a polyionic derivative of the medium—which polyionic derivative is at least said polysaccharide—and a quaternary ammonium salt, wherein at least one precipitation of the complex is performed on an inert porous support constituted of cellulose, an alkaline-earth metal salt substantially insoluble in water, aluminium oxide or hydroxide, silicon oxide, a silicate or an aluminosilicate. In Example 1 of the European patent application Celite® 545 (kieselguhr) and Cetavlon® (a cationic surfactant) are added to a fermentate containing bacterial polysaccharide. After 5 hours, a complex of polysaccharide/Cetavlon® and Celite® 545 is isolated by decanting the supernatant.

O. Adam et al. (*Anal. Biochem* 225 (1995), 321-327 describes a method for removing endotoxins from exopolysaccharides by temperature-induced Triton X-114 phase separation. D. Petsch & F. B. Anspach, *Journal of Biotechnology* 76 (2000), 97-119 describes a method for Triton X-114 based removal of endotoxins as well. The processes described in these papers have several disadvantages. Due to the heterogenic nature of the endotoxin and the equilibrium distribution of LPS in the liquid 2-phase systems, the final endotoxicity reduction of the alginate is limited. Furthermore, the method is not suitable for processing viscous fluids unless very high centrifugal forces are applied to separate the phases. Finally, it is very difficult to quantitatively separate the upper liquid phase from the lower liquid phase, making the process not very robust.

SUMMARY OF THE INVENTION

The inventors have developed a particularly robust method for reducing LPS levels in biopolymers. The method of the present invention can be operated on standard equipment. Furthermore, the present method can advantageously be employed to achieve in excess of 4 log reductions in LPS levels, resulting in endotoxin levels that are sufficiently low (well below 30 Endotoxin Units/g) to render it possible to use the treated biopolymers in surgery, including cranial and spinal surgery. The method of the present invention is characterised in that it comprises the successive steps of:
a) providing an aqueous solution containing 0.05-50 wt. % of dissolved LPS-containing biopolymer material; 0.001-10 wt. % of a surfactant; 0.05-15 wt. % of solid adsorbent and at least 50 wt. % of water;
b) allowing the adsorbent to adsorb LPS;
c) separating the solid adsorbent containing adsorbed LPS from the remaining aqueous solution; and
d) recovering the biopolymer material containing a reduced level of LPS from the separated aqueous solution.

Cranial and spinal implants have to meet the highest standards in terms of LPS levels as any LPS present in these implants can leak into the intrathecal fluid, which is in direct contact with the brain (no blood-brain barrier). In the USA cranial and spinal drugs and implants may contain not more than 14 Endotoxin Units (EU) per device. The ultra-low LPS-content of the biopolymers obtained by the present method makes it possible to employ these biopolymers in medical devices (e.g. sealants) for spinal surgery (e.g. single-level posterior lumbar laminectomy or laminotomy procedures to decrease postoperative epidural scarring) or cranial surgery (e.g. sealing of the dura after surgery by applying sealant over sutures to prevent leakage of cerebrospinal fluid). Medical devices containing ultra-pure biopolymers (e.g. alginates) obtained by the present method can be applied in spinal or cranial surgery without the risk of exceeding the aforementioned upper limit of 14 Endotoxin Units.

Although the inventors do not wish to be bound by theory, it is believed that the surfactant employed in the present method causes break-up of LPS aggregates which typically have a size of approximately 1 MDa. The break-up of these aggregates greatly facilitates the effective isolation of the LPSs in accordance with the present invention. In addition, unlike the 2-phase liquid extraction systems of the prior art, the present method employs a 3-phase extraction system in which equilibrium is pushed towards the solid phase, thereby enabling extraordinary reductions in LPS-levels to be achieved.

In the present method, the isolation of LPS from the biopolymer material is achieved by using a solid adsorbent to adsorb LPSs that have become dispersed in the aqueous phase. Isolation of the de-aggregated LPSs from the biopolymer and the aqueous phase is achieved in a very effective way by allowing the LPSs to become adsorbed onto the adsorbent and by subsequently removing the adsorbent by e.g. sedimentation, centrifugation or filtration. It was found that the solid adsorbent not only effectively removes LPSs from the biopolymer solution, but also the surfactant.

In order to achieve very high reductions in LPS levels the aforementioned sequence of steps a) to c) may be repeated several times until the LPS content of the biopolymer has been reduced to the desired level.

DETAILED DESCRIPTION OF THE INVENTION

Accordingly, the present invention relates to a method of reducing LPS levels in a LPS containing biopolymer material, comprising the successive steps of:
a) providing an aqueous solution containing 0.05-50 wt. % of dissolved LPS-containing biopolymer material; 0.001-10 wt. % of a surfactant; 0.05-15 wt. % of solid adsorbent; and at least 50 wt. % of water;
b) allowing the adsorbent to adsorb LPSs;
c) separating the solid adsorbent containing adsorbed LPSs from the remaining aqueous solution; and
d) recovering the biopolymer material containing a reduced level of LPS from the separated aqueous solution.

The term "biopolymer" as used herein refers to a special class of polymers produced by living organisms in which the monomer units are sugars, amino acids, and nucleic acids. Examples of biopolymers include polysaccharides, polypeptides and polynucleotides.

In the present method the LPSs can be adsorbed directly and/or indirectly by the solid adsorbent. Indirect adsorption can occur, for instance, if an LPS-containing surfacant phase is bound by the solid adsorbent. Because of the amphiphilic nature of surfactants and many LPSs, the present method can suitably employ hydrophilic (e.g. clays) as well as hydrophobic adsorbents (e.g. activated carbon) to remove LPSs, Various bioassays are available for measuring LPS levels, such as the rabbit pyrogen test (Pharmacopeia of the U.S. (1960) $16^{th}$ revision, p. 887. Mack Printing Co., Easton, Pa.) and the Limulus amoebocyte lysate (LAL) assay (F. C. Pearson et al., *J. Clin Microbiol.* 21 (1985), 865-868), the chicken embryo lethality assay (R. T. Smith, and L. Thomas, *J. Exp. Med.* 104 (1956) 217-231), and the galactosamine-primed mice lethality test (C. Galanos et al., *Proc. Natl. Acad. Sci.*

USA 76 (1979), 5939-5943.). The LAL assay is very sensitive and economical. A sensitivity of 0.02 EU ml$^{-1}$ can be accomplished with this assay (endpoint method). The LAL kinetic turbidimetric assay can suitably be used if even higher sensitivity is required (J. F. Remillard et al., *Prog Clin Biol Res.* 231 (1987) 197-210), and particularly applies to plate screenings.

According to a particularly preferred embodiment of the present invention, the surfactant employed in the present method is a liquid micelle-forming surfactant, more particularly a micelle-forming surfactant that can suitably be used to perform a micellar phase separation or cloud point extraction (CPE) to remove the LPSs from the aqueous biopolymer solution. Accordingly, the present method advantageously employs an aqueous solution containing a micelle-forming surfactant in a concentration exceeding the critical micelle concentration, which aqueous phase is caused to phase separate into an aqueous phase and a surfactant phase prior to the separation of the solid adsorbent from the remaining aqueous phase. The use of cloud point extraction in the present method offers the important advantage that that little or no surfactant residue is retained in the recovered LPS-free biopolymer material. The inventors have found that, if an adequate amount of solid adsorbent is employed, not only the phase separated (dispersed) surfactant but also dissolved surfactant are removed surprisingly effectively by the adsorbent. Thus, no additional clean-up operations are necessary to remove traces of surfactant from the recovered biopolymer material.

Cloud point extraction makes use of the fact that at low surfactant concentrations above the critical micelle concentration, micellar solutions of e.g. nonionic or slightly polar surfactants can exist as homogeneous isotropic liquid phases. Phase separation can be induced in this concentration range, for instance, by increasing temperature to the temperature at which the surfactant looses its water solubility ("cloud point"). In many such phase separations, the single isotropic micellar phase separates into two isotropic phases, both of which may contain surfactant, but which differ in total surfactant concentration. In the surfactant micellar-rich phase will be concentrated any hydrophobic organic components originally present in the sample subjected to the phase separation step.

The "criticial micelle concentration", unless indicated otherwise, is defined as the concentration at which surfactants in free solution are in equilibrium with surfactants in aggregated form. The self-organisation of the molecules of a surfactant depends on the concentration of the surfactant present in solution. Below the critical micelle concentration the surfactants form a single layer on the liquid surface and are dispersed in solution. At the first critical micelle concentration (CMC-I), the surfactant organises in spherical micelles, at the second critical micelle concentration (CMC-II) into elongated pipes, and at the lamellar point (LM or CMC-III) into stacked lamellae of pipes.

In the cloud point extraction method of the present invention any micelle-forming surfactant can be used, provided it is feasible to induce phases separation of the micellar solution. Advantageously, the present method employs a micelle-forming surfactant that upon phase separation forms droplets with a density that exceeds the density of the aqueous biopolymer phase. Thus, it can be ensured that under the influence of gravity and/or centrifugal force both the surfactant phase and the solid adsorbent will accumulate as a sediment that can easily be separated by means of e.g. simple decanting. Accordingly, in accordance with a preferred embodiment, at the "cloud point temperature", the micelle-forming surfactant has a density in excess of 1.03 g/ml, preferably in excess of 1.05 g/ml.

Phase separation of the micellar aqueous solution into an aqueous phase and a surfactant phase is preferably induced by submitting the solution to temperature increase, salt addition, pH change and/or osmotic stress. Most preferably, phase separation is achieved by increasing the temperature of the aqueous solution. According to a particularly preferred embodiment of the present method, the micellar aqueous solution has a temperature in the range of 0-99° C., more preferably in the range of 5-95° C. and phase separation is induced by increasing this temperature by at least 5° C., preferably by at least 10° C.

Preferably, the surfactant employed in the present method is an non-ionic or anionic polysaccharide. According to a particularly preferred embodiment, the surfactant is a non-ionic surfactant. Non-ionic surfactants offer the advantage that phase separation can be achieved relatively easily, e.g. by increasing temperature. Examples of non-ionic micelle-forming surfactants that may suitably be employed are:

alkylphenol ethoxylates represented by the formula $C_xH_{2x+1}$—$C_6H_4$—O—$(C_2H_4O)_n$H, wherein:
x is within the range of 4-12; and
n is within the range of 4-12 nonylphenoxypolyethoxyethanols represented by the formula $C_{15}H_{24}O(C_2H_4O)_n$, wherein n is within the range of 3-40, preferably within the range of 4-30 polyethylene glycol sorbitan monoesters of fatty acids having a chain length of 12-18 carbon atoms (TWEEN), preferably $CH_3(CH_2)_{10}CO_2^-$ (laureate) or 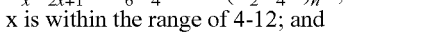 $CH_3(CH_2)_7C_2H_2(CH_2)_7CO_2^-$ (oleate)

3-([3-Cholamidopropyl]dimethylammonio)-2-hydroxy-1-propanesulfonate (CHAPSO)

As regards the nonylphenoxypolyethoxyethanols (nonoxynol), nonoxynol-4 (n=4), nonoxynol-15 (n=15) and nonoxynol-30 (n=30) are particularly preferred.

Most preferably, the micelle-forming surfactant is an alkylphenol ethoxylate as defined herein before, wherein x=8 and 7≦n≦10. Examples of such alkylphenolethoxylates are octylphenol ethoxylates, such as Triton X-114 and Triton X-100.

The amount of surfactant employed in the aqueous starting solution typically is within the range of 0.01-10 wt. %. Preferably, the surfactant is employed in the aqueous solution in a concentration within the range of 0.1-5 wt. %, most preferably within the range of 0.5-2 wt. %.

An important advantage of the present method resides in the fact that it can be used to process concentrated, highly viscous aqueous biopolymer solutions. Accordingly, in a preferred embodiment of the present process, the separated aqueous phase has a kinematic viscosity of at least 100 cSt at 20° C. Even more preferably, the kinematic viscosity at 20° C. is at least 500 cSt. Most preferably, said viscosity is at least 2500 cSt. Usually, the kinematic viscosity of the separated aqueous phase does not exceed 15000 cSt at 20° C. The kinematic viscosity may suitably be determined with a U-tube Reverse flow viscometer or a Synchro-Lectric rotational viscometer.

The solid adsorbent employed in the present process is insoluble in the aqueous solution and has to be capable of directly or indirectly adsorbing LPS. Preferably, the solid adsorbent is capable of adsorbing the surfactant that is used in the present method as this will help to avoid contamination of the treated biopolymer material with traces of surfactant. Examples of solid adsorbents that may suitably be employed include of activated carbon, adsorbent clays and combinations thereof. Examples of adsorbent clays include: aluminium phyllosilicate, montmorillonite (and other smectite group minerals), sepiolite, dicalite, perlite, diatomite, kaolinite, illite, zeolite, diatomaceous earth and combinations thereof. Most preferably, the adsorbent clay is adsorbent aluminium phyllosilicate.

Particularly good results are obtained in case a hydrophobic adsorbent, such as activated carbon, is employed as the adsorbent material. Hence, according to one preferred embodiment, the solid adsorbent comprises activated carbon. Even more preferably, the adsorbent is activated carbon.

According to another preferred embodiment, the solid adsorbent is a clay (e.g. an absorbent aluminium phyllosilicate). Clays offer the advantage that they sediment rapidly and that virtually no residual adsorbent remains in suspension. Furthermore, the inventors have observed that these minerals are a very effective adsorbent of both dispersed and dissolved surfactant. This observation is confirmed by the findings of A. G. Epantaleón et al., *Use of activated clays in the removal of dyes and surfactants from tannery waste waters*, Applied Clay Science 24 (2003) 105-110.

Another advantageous property of clays is their capability to drag along dispersed droplets and/or dispersed particles. Thus, when a layer of these adsorbents is introduced near the surface of the aqueous biopolymer solution, said adsorbent layer will gradually descend to the bottom of the container holding the solution whilst simultaneously 'filtering out' any dispersed material, such as activated carbon particles or surfactant droplets.

It was found that the combined use of a hydrophobic adsorbent and an adsorbent clay, such as aluminium phyllosilicate, enables very effective removal of the surfactant. Although the inventors do not wish to be bound by theory, it is believed that, especially if separation of the solid adsorbent is achieved by prolonged centrifugation, the adsorbent clay forms the top layer of the sediment and seals off the underlying hydrophobic adsorbent as well as the surfactant adsorbed onto said hydrophobic adsorbent. As a result contamination of the supernatant during e.g. decanting is minimised effectively.

In a preferred embodiment, the solid adsorbent employed in the present method is a microporous adsorbent. The use of a microporous adsorbent offers the advantage that an exceptionally high surface area is obtained, which is required to magnify the relatively weak "London dispersion forces". The microporous solid adsorbent employed in the present method preferably has a microporosity (MPV) of at least $0.02\ cm^3 g^{-1}$, most preferably of at least $0.25\ cm^3 g^{-1}$ and a BET surface area ($S_{BET}$) of at least $100\ m^2 g^{-1}$, most preferably of at least $800\ m^2 g^{-1}$.

The use of an excess amount of solid adsorbent offers the important advantage that, in case of cloud point extraction, the surfactant phase is essentially completely adsorbed onto the adsorbent material, thus forming a solid mass that can be separated very easily by solid-liquid separation techniques well-known to a person skilled in the art. Preferably, the solid adsorbent containing the adsorbed surfactant phase is heavier than the aqueous biopolymer phase, so that it will settle under the influence of gravity and/or centrifugal force.

In the present method the surfactant concentration in the aqueous solution remaining after separation of the solid absorbent is at least 50 times, preferably at least 2500 times lower than the surfactant concentration in the aqueous starting solution. Typically the surfactant concentration in the aqueous solution remaining after separation is less than 200 mg/kg, most preferably less than 4 mg/kg.

The inventors have observed that the solid adsorbent material, after having adsorbed the surfactant phase, forms a kind of cake sediment that can easily be removed by, for instance, centrifugation or filtration. However, in particular if the solid adsorbent contains very small particles (e.g. in case of activated carbon) and/or in case the aqueous biopolymer solution is very viscous, these very fine particles may remain suspended in the aqueous phase even after separation of the surfactant phase.

Unexpectedly, it was found that activated carbon can be removed quantitatively by adding an adsorbent clay before separation of the aqueous phase from the surfactant phase. Virtually quantitative removal of very small adsorbent particles is achieved even if the aqueous phase is highly viscous. In contrast, well-known solid-liquid separation techniques, such as filtration and centrifugation, are not suitable for achieving quantitative removal of adsorbent particles from viscous biopolymer solutions. Furthermore, it was found that the combined use of activated carbon and adsorbent clay enables virtually complete removal of LPSs. Thus, according to a preferred embodiment, the separation of the aqueous phase from the surfactant phase comprises the addition of activated carbon and adsorbent clay. Most preferably, the clay employed in the present method is a swelling clay. Non-swelling clays are less suitable, especially if the present method is used to process biopolymers whose gelation is triggered by di- or tri-valent cations.

The adsorbent clay is advantageously employed in the present method in an amount in excess to the activated carbon. Most preferably, the adsorbent clay is employed in an amount of 50% by weight in excess of the activated carbon. Expressed differently, the adsorbent clay is preferably employed in an amount of 1-10 wt. %, more preferably in an amount of 2-4 wt. %, by weight of the aqueous solution.

In the present method the solid adsorbent may be incorporated in the aqueous solution at different stages. In principle, the adsorbent may be dispersed into water even before the surfactant is added. Preferably, however, the adsorbent is added to the solution after the surfactant has been added, and in case of a micelle-forming surfactant is employed, after phase separation in the surfactant phase and aqueous phase has occurred.

Typically, the solid adsorbent is employed in the present method in an amount of 50-1000% by weight of the separated surfactant phase. Preferably, the adsorbent is employed in an amount of 100-300% by weight of the separated surfactant phase. Expressed differently, the adsorbent is advantageously employed in an amount of 0.1-10% by weight of the aqueous solution. Most preferably, the amount of adsorbent employed is within the range 1-3% by weight of the aqueous solution.

As mentioned herein, before the present method may advantageously be employed to remove LPSs from biopolymer material. Examples of biopolymer material that can advantageously be processed in accordance with the present invention include: polysaccharides such as alginate, xanthan gum, gellan gum, microbial-derived cellulose and hyaluronates; proteins, such as gelatine, collagen, enzymes and antibodies; and polynucleotides. According to a preferred embodiment, the biopolymer material is of microbial origin. For the purpose of this invention biopolymers produced by recombinant micro-organisms are also regarded as biopolymers of microbial origin.

Examples of biopolymers of microbial origin that may suitably be depyrogenated by means of the present method include alginate, xanthan gum, gellan gum, or microbial-derived cellulose and combinations of these biopolmers. According to a particularly preferred embodiment the biopolymer of microbial origin is an alginate salt, preferably sodium alginate.

The present method is particularly suited for depyrogenating alginates with a particularly high molecular weight. Accordingly, in another preferred embodiment, at least 80 wt. % of the LPS containing alginate has a molecular weight of least 10 kDa (i.e. at least 50 monomeric subunits).

Typically, the aqueous solution employed in the present process contains from 0.1-50 wt. % of the biopolymer material. As explained herein before, the advantages of the present method are particularly pronounced in case the aqueous solution contains a high level of biopolymer material as the present method can suitably be used to depyrogenate highly viscous solutions. Accordingly, in a particularly preferred embodiment, the aqueous solution contains at least 1 wt. % of the biopolymer material.

In the method according to the present invention the separation of the aqueous phase from the surfactant phase is suitably achieved by removing the solid adsorbent containing the adsorbed surfactant phase and LPS. Said adsorbent can be removed from the aqueous phase using solid-liquid separation methods well known in the art, e.g. centrifugation, sedimentation, filtration etc.

After removal of solid adsorbent, the biopolymer material may be separated from the aqueous phase using a variety of methods including precipitation, crystallisation and drying. According to a particularly preferred embodiment, the biopolymer material is isolated from the separated aqueous by means of precipitation. Even more preferably, the recovery of the biopolymer material from the separated aqueous phase involves precipitation of the biopolymer material by adding at least 10% by weight of water of an organic solvent that is miscible with water. Examples of organic solvents that may suitably be employed include primary $C_{1-3}$ alcohols, $C_{2-4}$ diols, $C_{3-4}$ triols, 2-propanol, $C_{2-3}$ ketonese and combinations thereof. Preferably, the organic solvent is selected from the group consisting of ethanal, n-propanol, i-propanol, acetone and combinations thereof. Most preferably, the organic solvent employed is ethanol.

The inventors have found that the organic solvent can be removed very efficiently from the precipitated biopolymer material by isolating the precipitate and subsequently drying it by extracting it with a liquefied gas, a subcritical gas or a supercritical gas. The term "subcritical gas" as used herein refers to a compressed gas that is neither in a supercritical or liquefied state but that has been pressurised to at least 10 bar, preferably to at least 20 bar. Preferably, the supercritical, subcritical or liquefied gas has a pressure of at least $0.3 \times P_c$ and a temperature of at least $T_c$-60° C., $P_c$ representing the critical pressure of the gas and $T_c$ representing the critical temperature of the gas. In the present process, the gas used to extract the organic solvent preferably has a pressure of at least 10 bar, even more preferably of at least 20 bar The liquefied, subcritical or supercritical gas is advantageously selected from the group consisting of carbon dioxide, nitrous oxide, ethane, ethylene propane, cyclopropane, propylene, butane, argon, nitrogen and combinations thereof. Most preferably, the gas employed to dry the precipitate is carbon dioxide.

As mentioned herein before, the present method can advantageously be used to reduce the LPS levels of biopolymers to trace levels or even less. Typically, the recovered biopolymer material obtained from the present process contains less than 100 LPS units per gram of biopolymer material, more preferably less than 10 LPS units per gram of biopolymer material. The reduction in LPS level achieved in the present process typically exceeds a factor $10^{2.5}$. Even more preferably, the reduction in LPS level achieved in the present process exceeds a factor $10^3$. Most preferably, the latter reduction factor exceeds $10^{3.5}$.

The present method is particularly suited for removing lipid A containing lipopolysaccharides. Accordingly, in a preferred embodiment of the invention, the lipid A content of the recovered biopolymer material is at least $10^{2.5}$ times lower, more preferably at least $10^3$ times lower and most preferably at least $10^{3.5}$ times lower than the lipid A content of the biopolymer starting material.

As explained herein before, the present invention enables the manufacture of ultra-pure biopolymers in which LPS levels have been reduced to such an extremely low level that they can be used in medical devices for spinal or cranial surgery. Thus, the present invention enables the preparation of medical devices, such as sealants, that can be used in spinal or cranial surgery. Accordingly, another aspect of the invention relates to a system for delivering a surgical sealant that comprises an ultrapure alginate that upon use in cranial or spinal surgery introduces not more than 14 Endotoxin Units. More particularly, this present system for delivering a surgical sealant comprises:

- a first reservoir comprising a first flowable composition in the form of an aqueous solution of an ionically cross-linkable alginate;
- a second reservoir comprising a second flowable composition;
- a first outlet from the first reservoir;
- a second outlet from the second reservoir,
- said first outlet and said second outlet being arranged in such a way that the first flowable composition is mixed with the second flowable composition when both compositions are simultaneously expelled from the respective reservoirs;

wherein upon admixture of the first flowable composition with the second flowable composition a solid or semi-solid ionically cross-linked alginate gel is formed, said system further being characterised in that the first flowable composition and the second flowable composition together contain not more than 14 Endotoxin Units.

It is crucial that upon admixture of the first flowable composition with the second flowable composition gelation will occur relatively slowly in other to allow the gel to form in situ. In order to achieve this, the present delivery system can suitably employ a first flowable composition containing alginate and a sequestrant and a second flowable composition containing a multivalent metal cation. The sequestrant can bind the multivalent metal cations, thereby reducing the rate at which the alginate is cross-linked when the first flowable composition is combined with the second flowable composition. In an alternative embodiment the cross-linking rate is controlled by employing a first flowable composition containing alginate and undissociated multivalent metal cations and a second water free flowable composition containing a slow release acid such as gluconodeltalactone. After extrusion, the gradual pH reduction caused by the slow release acid will result in dissociation (dissolution) of the multivalent metal cation and subsequent cross-linking of the alginate by the dissociated multivalent metal cations.

Undissociated multivalent metal ions can be incorporated in the present delivery system in the form of non-dissolved salts, non-dissociated complexes or combinations thereof. Preferably, the undissociated multivalent metal cations are contained in the system in the form of non-dissolved salts.

Examples of multivalent metal ions that may suitably be used in the present system to cross-link the alginate are $Ca^{2+}$, $Mg^{2+}$ and combinations thereof.

As explained above, the present delivery system is designed to produce an alginate gel in situ after the first flowable composition has been combined with the second flowable composition. The delivery system may contain a mixing chamber that is connected to both the first and second outlet and that comprises another outlet (e.g. a cannula or a nozzle) for dispensing the combined compositions. Alternatively, the first outlet and second outlet may be arranged in such a way that the first flowable composition is automatically combined with the second composition when both compositions are simultaneously expelled from their respective reservoirs. This may be achieved, for instance, by employing concentrically arranged outlets or by an air or pressurised gas assisted spray.

According to a particularly preferred embodiment, the alginate employed in the present system for delivering a surgical sealant is an alginate obtained by a method as described herein before.

The alginate contained in the present delivery system advantageously contains less than 50 EU, more preferably less than 30 EU per gram.

The invention is further illustrated by means of the following examples.

EXAMPLES

Example 1

Sodium alginate was dissolved in distilled water to a final concentration of 2.5% (w/w) and a kinematic viscosity of 480 cSt. The kinematic viscosity was determined with a U-tube Reverse flow viscometer (Poutten Selfe & Lee BS/IP/RF size 3; c=0.03023). The endotoxicity was determined on 91,000 EU/g using a kinetic-turbidimetric assay from Associates of Cape Cod, Inc.

After addition of 1 vol. % of Triton X-114 (an octylphenol ethoxylate having a HLB of 12.3 and containing on average 7.5 ethoxylate residues) the suspension was stirred with a mixer for 30 minutes at a temperature just below the detergent's cloud point (i.e. 23° C. at 1% v/v). Subsequently 3 wt. % of adsorbent aluminium phyllosilicate (Montmorillonite, B-3378, ex Sigma-Aldrich) were dispersed into the suspension, which was brought to 70° C. and stirred for another 30 minutes.

Fifteen hundred ml's of the suspension so obtained were transferred to Sorvall Dry-spin bottles that were placed into a pre-heated (70° C.) Sorvall GSA fixed-angle rotor. After centrifugation for 60 min at 11,000 rpm (27,000×g) using a Sorvall RC-5B plus centrifuge the supernatant was quantitatively collected by decantation. The suspension was subsequently stirred for 30 minutes at room temperature and centrifuged for 60 minutes at 11,000 rpm. The resulting solution was decanted and brought to 60% ethanol by weight and allowed to settle for 30 min to let the alginate precipitate and decolour.

The clear white precipitate was collected and the fluid was squeezed out with a press. The gum-like precipitate was shredded and resuspended in absolute alcohol with the help of a blender. After 30 minutes of equilibration, the precipitate was collected with a sieve and compressed. The compressed product still contained around 75% (w/w) liquid material.

Next, the product was poured into a 4.2 litres autoclave (UHDE GmbH, Dortmund) that was heated to 95° C. by means of a jacket, using heating oil. Carbon dioxide was pressurised to 150 bar using a plunger pump (Orlita Prominent, Heidelberg) and heated to 95° C. before being pumped through the gel-like material at 300 g/min during 45 min. The product that formed within the vessel was collected on the filter at the bottom of the vessel. The product displayed a fibrous structure as confirmed by S.E.M. and had gained 10% viscosity (per gram of dried product). The final recovery was near to 85%. The endotoxicity of the final product was determined on 350-400 EU/g, which corresponds to a factor $10^{2.4}$ purification.

Example 2

Sodium alginate was dissolved in distilled water to a final concentration of 4.5% (w/w) and a kinematic viscosity of 2700 cSt. The endotoxicity was determined on 91,000 EU/g using a kinetic-turbidimetric assay from Associates of Cape Cod, Inc.

After addition of 1 vol. % of Triton X-114 the suspension was stirred with a mixer for 30 minutes at a temperature just below the detergent's cloud point (i.e. 23° C. at 1% v/v). Subsequently 2 wt. % of activated carbon (Norit SX plus; MPV 0.35 cm$^3$/g; $S_{BET}$ 1051 m$^2$/g) were dispersed into the suspension, which was brought to 70° C. and stirred for another 30 min.

Fifteen hundred ml's of the suspension so obtained were transferred to Sorvall Dry-spin bottles that were placed into a pre-heated (70° C.) Sorvall GSA fixed-angle rotor. After centrifugation for 60 min at 11,000 rpm (27,000×g) using a Sorvall RC-5B plus centrifuge the supernatant was quantitatively collected by decantation. At this stage, the intermediate product, essentially free of carbon, was found to have an endotoxicity of 600 EU/g.

Remaining traces of carbon in the supernatant were removed by suspending 3 wt. % of Montmorillonite (Sigma B-3378) and 1% of triton X-114 into the solution with a blender. The suspension was subsequently stirred for 30 minutes at room temperature and centrifuged for 60 min at 11,000 rpm. The resulting solution was decanted and brought to 60% ethanol by weight and allowed to settle for 30 min to let the alginate precipitate and decolour.

The clear white precipitate was collected and the fluid was squeezed out with a press. The gum-like precipitate was shredded and resuspended in absolute alcohol with the help of a blender. After 30 minutes of equilibration, the precipitate was collected with a sieve and compressed. The compressed product still contained around 75% (w/w) liquid material. Excess alcohol was removed from the squeezed product by extraction with supercritical carbon dioxide as carried out in example 1, with a 30 minutes reduced extraction time.

The essentially dry product was resolubilised in injection-grade water (sterile and apyrogenic, B. Braun, Melsungen A G, Germany) to a final concentration of 8.0%. The highly viscous fluid (15000 cSt) was transferred to a syringe pump (ISCO 260D, Teledyne Isco, Lincoln USA) at ambient temperature and sprayed into an autoclave via the 0.0013 cm$^2$ centre hole of a two-fluid co-axial nozzle at 3.3 ml/min. The carbon dioxide was sprayed around the centre hole through a 0.0122 cm$^2$ opening. The carbon dioxide was pressurised to 180 bar using a plunger pump (Orlita Prominent, Heidelberg) and heated to 95° C. before being sprayed at 600 g/min. The autoclave (UHDE GmbH, Dortmund) was also heated to 95° C.

The powder that formed within the vessel was collected on the filter at the bottom of the vessel. S.E.M. revealed small aggregates of global structures with a predominant cross diameter of less than 5 μm. The endotoxicity of the final product was determined on 25 EU/g, which corresponds to a factor $10^{3.6}$ purification.

Example 3

Example 1 was repeated, except that Triton X-114 was replaced by 0.1 wt. % of sodium dodecyl sulfate (Sigma L6026). Furthermore, as phase partitioning does not occur with this solid, ionic detergent, the operating temperature was room temperature. Also, the alginate concentration had to be lowered to 1.8% (185 cSt) in order to facilitate the centrifugal removal of the activated carbon.

After alcohol precipitation, the product was dried as described in example 2. Although a $10^3$ decrease in endotixicity was obtained, the product still required an additional cleaning step to remove residual sodium dodecyl sulfate.

Example 4

A hot (90° C.) aqueous solution of gelatine (13,200 EU/g; 30% w/w) was prepared. The solution was temporarily chilled to just below the cloud point of Triton X-100 (an octylphenol ethoxylate comprising on average 9.5 ethoxylate residues and having an HLB of 13.4). Subsequently, 1 vol.% volumes of Triton X-100 were added. After stirring for 5 minutes, the suspension was heated to 90° C. to induce phase separation. Subsequently, 2 wt. % of pre-washed activated carbon (Norit SX plus) was dispersed into the suspension. Pre-washing the Norit served the removal of the smallest particles.

The suspension temperature was maintained at 80° C. and stirred for 30 min. Three litres of the suspension were transferred to containers that were placed into a pre-heated (80° C.) Beckmann JA-10 fixed-angle rotor. After 30 min centrifugation at 10,000 rpm (17,700×g) in a Beckman J2-21 superspeed centrifuge the supernatant was gently decanted. Traces of carbon were removed by filtering the hot solution on apyrogenic glass wool that was placed on top of a sand-covered filter.

The clarified hot solution was transferred to a syringe pump (ISCO 260D, Teledyne Isco, Lincoln USA) that carried a heating jacket. The solution was sprayed at 90° C. into a 4 litre UHDE-autoclave through the 0.0013 cm$^2$ centre hole of a two-fluid co-axial nozzle at 2.5 ml/min. The vessel was pressurised with carbon dioxide to 150 bar using a plunger pump (Orlita Prominent, Heidelberg) and heated to 90° C. before being sprayed at 500 g/min. The carbon dioxide was sprayed around the centre hole through a 0.0122 cm$^2$ opening. The powder that formed within the vessel was collected on the filter at the bottom of the vessel.

The endotoxicity reduction turned out to be a factor $10^{2.1}$, as determined with the kinetic-turbidimetric assay from Associates of Cape Cod, Inc.

Example 5

Danisco Grindsted PHU-156 sodium alginate (525 KDa, 40 wt. % guluronate) was dissolved in reversed osmosis water to a final concentration of 1.9% (w/w) and a kinematic viscosity of 5,500 cSt. The kinematic viscosity was determined through curve fitting with extrapolation using a U-tube Reverse flow viscometer (Poutten Selfe & Lee BS/IP/RF size 3; c=0.03023). The endotoxicity was determined on 110,000 EU/g using a kinetic-turbidimetric assay from Associates of Cape Cod, Inc (further referred to as "the gel-clot method").

After addition of 1 wt. % of Triton X-114 the suspension was stirred with a mixer for 30 minutes at a temperature 10 degrees below the detergent's cloud point (i.e. 23° C. at 1% v/v). After increasing the temperature at least 10 degrees beyond the cloud point 1.5 wt. % of activated carbon (Norit SX plus; MPV 0.35 cm$^3$/g; $S_{BET}$ 1051 m$^2$/g) were dispersed into the suspension, which was brought to 70° C. and stirred for another 30 min. Subsequently 2.25 wt. % of Montmorillonite ((Sigma B-3378) were dispersed into the suspension and stirring was continued for another 30 minutes at 70° C.

The 6 litres of suspension so obtained was transferred to 1-litre polypropylene bottles that were placed into a JLA-8.1000 fixed-angle rotor. After centrifugation for at least 12 hours at 7,000 rpm (12,300×g) using a Beckman Avanti J-26 XP High Performance Centrifuge the supernatant was quantitatively collected by decantation. The resulting solution was brought to 50% ethanol by volume, blendered and allowed to settle for at least 1h to let the alginate precipitate and decolour.

The clear white precipitate was concentrated on a sieve. The gum-like precipitate was further compressed by centrifugation at room temperature for 30 min's at 5000 RPM in the above described centrifuge. The white precipitate was shredded and resuspended in absolute alcohol with the help of a blender. After 30 minutes of equilibration, the precipitate was collected with a sieve and compressed by repeated centrifugation (30 min's at 5000 RPM). The compressed product still contained around 75% (w/w) liquid substance.

Next, the product was poured into a 4.2 litres autoclave (UHDE GmbH, Dortmund) that was heated to 95° C. by means of a jacket, using heating oil. Carbon dioxide was pressurised to 150 bar using a plunger pump (Orlita Prominent, Heidelberg) and heated to 95° C. before being pumped through the gel-like material at 300 g/min during 45 min. The product that formed within the vessel was collected on the filter at the bottom of the vessel. The product displayed a fibrous structure as confirmed by S.E.M. and had gained 10% viscosity (per gram of dried product). The final recovery was near to 75%. The endotoxicity of the final product was determined as <30 EU/g, which lies below the detection limit.

Example 6

ISP Manugel DMB sodium alginate (150 Kda, 63 wt. % guluronate) was dissolved in reversed osmosis water to a final concentration of 2.8% (w/w) and a dynamic viscosity of 6,000 mPa·s. The viscosity was measured at various concentrations alginate (ranging from 0.4-3%) in saline using a Synchro-Lectric rotational viscometer (Brookfield Engineering Laboratories Inc., MA) operated at 20° C. The endotoxicity was determined on $1.1*10^6$ EU/g using the gel-clot method.

The solution was treated exactly as described in example 5 until the stage where the clear white precipitate was collected and the fluid was squeezed out with a press. The gum-like precipitate was shredded and resuspended in 6 litres of a 1:1 mixture of absolute ethanol and injection-grade water (sterile and apyrogenic, B. Braun, Melsungen A G, Germany) for extended decoloration during another hour. After repeated equilibration in absolute alcohol the precipitate was collected with a sieve and compressed. The compressed product still contained around 75% (w/w) liquid material. Drying was performed as described in example 1. The final recovery was near to 70%. The endotoxicity of the final product was determined as 60 EU/g, corresponding to a purification factor of 4.3 log.

Example 7

ISP Manucol LD sodium alginate (low MW, 39 wt. % guluronate) was dissolved in reversed osmosis water to a final concentration of 24.0 wt. % The endotoxicity was determined on $4.3*10^4$ EU/g using the gel-clot method.

The solution was treated exactly as described in example 6 with the exception that reversed osmosis water (instead of injection grade water) was used for equilibration. The final recovery was 72%. The endotoxicity of the final product was $2*10^3$ EU/g, indicating that a highly purified water must be employed during equilibration in order to maximise depyrogenisation levels. The purified sample was also analyzed on possible traces of Triton X-114. To this end the sample was subjected to TLC and refractive index-measurements (P. Strop & A. T. Brunger (2005) *Protein Sci.* 14, 2207-2211), parallelled by direct UV spectroscopy. Levels of Triton X-114 were traced at a concentration of 0.01-0.02% which is well below the specification of 0.1%.

The invention claimed is:

1. A method of reducing lipopolysaccharide levels in a lipopolysaccharide containing alginate, said method comprising:
   (a) providing an aqueous solution containing 0.05-50 wt. % of dissolved lipopolysaccharide-containing alginate; 0.001-10 wt. % of a surfactant; 0.05-15 wt. % of solid adsorbent; and at least 50 wt. % of water;
   (b) allowing the solid adsorbent to adsorb lipopolysaccharides;
   (c) separating the solid adsorbent containing adsorbed lipopolysaccharides from the remaining aqueous solution by means of centrifugation, sedimentation or filtration; and
   (d) recovering the alginate containing a reduced level of lipopolysaccharide from the separated aqueous solution.

2. The method according to claim 1, in which the separating is by means of centrifugation, sedimentation, filtration, or a combination thereof.

3. The method according to claim 1, wherein the surfactant is a micelle-forming surfactant in a concentration exceeding the critical micelle concentration.

4. The method according to claim 3, wherein the micelle-forming surfactant has a density in excess of 1.03 g/ml at the cloud point temperature.

5. The method according to claim 3, wherein prior to (c), said aqueous solution is caused to phase separate into an aqueous phase and a surfactant phase.

6. The method according to claim 3, wherein the micelle-forming surfactant is an alkylphenol ethoxylate represented by the formula $C_xH_{2x+1}$—$C_6H_4$—O—$(C_2H_4O)_n$H, wherein:
   x is within the range of 4-12; and
   n is within the range of 4-12.

7. The method according to claim 1, wherein the separated aqueous phase has a viscosity of at least 100 cSt at 20° C.

8. The method according to claim 1, wherein the solid adsorbent is selected from the group consisting of activated carbon, clays and combinations thereof.

9. The method according to claim 8, wherein the solid adsorbent comprises activated carbon.

10. The method according to claim 8, wherein the solid adsorbent comprises an adsorbent clay.

11. The method according to claim 5, wherein the phase separation is induced by increasing temperature, adding salt, changing pH and/or osmotic stress.

12. The method according to claim 1, wherein the alginate is sodium alginate.

13. The method according to claim 1, wherein the recovering (d) comprises precipitating the alginate by adding at least 10% by weight of water of an organic solvent that is miscible with water.

* * * * *